(12) United States Patent
Nakamura et al.

(10) Patent No.: US 8,211,820 B2
(45) Date of Patent: Jul. 3, 2012

(54) CATALYST COMPOSITION, AND PROCESS FOR PRODUCTION OF CROSS-COUPLING COMPOUND USING THE SAME

(75) Inventors: Masaharu Nakamura, Uji (JP); Takuji Hatakeyama, Uji (JP)

(73) Assignees: Kyoto University, Kyoto-shi (JP); Tosoh Finechem Corporation, Shunan-shi (JP)

( * ) Notice: Subject to any disclaimer, the term of this patent is extended or adjusted under 35 U.S.C. 154(b) by 283 days.

(21) Appl. No.: 12/529,297

(22) PCT Filed: Mar. 3, 2008

(86) PCT No.: PCT/JP2008/053751
§ 371 (c)(1),
(2), (4) Date: Aug. 31, 2009

(87) PCT Pub. No.: WO2008/111414
PCT Pub. Date: Sep. 18, 2008

(65) Prior Publication Data
US 2010/0094018 A1   Apr. 15, 2010

(30) Foreign Application Priority Data
Mar. 9, 2007  (JP) .................... 2007-60926

(51) Int. Cl.
  *B01J 31/02* (2006.01)
  *C07C 1/26* (2006.01)
  *C07C 17/00* (2006.01)
  *C07D 213/06* (2006.01)

(52) U.S. Cl. ........ 502/158; 502/167; 546/348; 570/143; 585/446

(58) Field of Classification Search ........................ None
See application file for complete search history.

(56) References Cited

U.S. PATENT DOCUMENTS

| 2003/0158419 | A1 | 8/2003 | Kamikawa et al. |
| 2003/0162950 | A1 | 8/2003 | Itahashi et al. |
| 2006/0111593 | A1 | 5/2006 | Itahashi et al. |
| 2006/0122398 | A1 | 6/2006 | Karch et al. |
| 2007/0123734 | A1 | 5/2007 | Nakamura et al. |
| 2010/0185019 | A1* | 7/2010 | Nakamura et al. ............ 568/642 |

FOREIGN PATENT DOCUMENTS

| JP | 04-173756 A | 6/1992 |
| JP | 2000-095713 A | 4/2000 |
| JP | 2000-229243 A | 8/2000 |
| JP | 2003-212798 A | 7/2003 |
| JP | 2004-091465 A | 3/2004 |
| JP | 2005-534711 A | 11/2005 |
| JP | 2006-151947 A | 6/2006 |
| JP | 2006-231318 A | 9/2006 |
| WO | WO 2005/075384 A1 | 8/2005 |

OTHER PUBLICATIONS

Furstner, et al., J. Am. Chem. Soc., 124(46): 13856-13863 (2002).
Hatakeyama et al., J. Am. Chem. Soc., 129(32): 9844-9845 (2007).
Miyaura et al., Chemical Reviews, 95(7): 2457-2483 (1995).
Tamao et al., J. Am. Chem. Soc., 94(12): 4374-4376 (1972).

* cited by examiner

*Primary Examiner* — Kamal Saeed
(74) *Attorney, Agent, or Firm* — Leydig, Voit & Mayer, Ltd.

(57) ABSTRACT

The invention provides a catalyst composition for use in a cross-coupling reaction containing an iron or cobalt fluoride and a nitrogen-containing heterocyclic ring compound represented by General Formula (1A) or (1B),

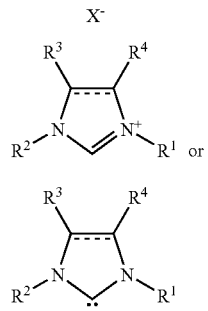

wherein $R^1$ and $R^2$ are same or different, and represent substituted or unsubstituted aryl group etc.; and $R^3$ and $R^4$ are same or different, and represent hydrogen etc., ------ represents a single bond or a double bond, and $X^-$ represents a monovalent anion. The invention also provides a method for producing a cross-coupling compound by reacting an organic magnesium compound with an organic halogen compound in the presence of the catalyst composition.

20 Claims, No Drawings

CATALYST COMPOSITION, AND PROCESS FOR PRODUCTION OF CROSS-COUPLING COMPOUND USING THE SAME

TECHNICAL FIELD

The present invention relates to a catalyst that is significantly useful for cross-coupling reactions, which are important in the field of organic synthetic chemistry; and to a production method for a cross-coupling compound using the catalyst. The method of the present invention enables the efficient production of non-symmetrical biaryl compounds and the like, which are useful for liquid crystalline materials and medical intermediates.

BACKGROUND ART

Because of their stability, electronic properties and fixed molecular structure, which are all derived from the aromatic ring, non-symmetrical biaryl compounds are significantly useful as electronic industry materials, medicines, agricultural chemicals, various functional compounds, and synthetic intermediates of these.

A known method of selective production of non-symmetrical biaryl compounds involves conducting a cross-coupling reaction of an organic boron compound with an organic halogen compound in the presence of a palladium catalyst (Non-patent Literature 1, Patent Literature 1). However, the palladium catalyst and the material, i.e., the organic boron compound, used in this method are both expensive. Therefore, this method is not desirable as an industrial production method. In addition, there is an environmental restriction due to the recent establishment of a boron discharge standard.

Another known cross-coupling method, which carries out a cross-coupling reaction of an organic magnesium compound and an organic halogen compound, does not require as high a cost (Non-patent Literature 2, Patent Literature 2, and Patent Literature 3). This method, which employs an inexpensive organic magnesium compound, generally uses a nickel catalyst or a palladium catalyst. However, nickel catalysts are usually highly toxic, and palladium catalysts are expensive. Therefore, this method ds also not desirable as an industrial production method.

A recent publication disclosed a synthetic method that carries out a cross-coupling reaction of an organic magnesium compound and an organic halogen compound using a safe and inexpensive iron catalyst (Non-patent Literature: 3). Non-patent Literature 3 teaches that the use of iron chloride or acetylacetonato iron as a catalyst ensures a high yield of the reaction of an alkyl magnesium compound and an aryl chloride compound. However, the method of Non-patent Literature 3 is still incapable of carrying out the synthesis of the non-symmetrical biaryl compounds useful for liquid crystalline materials or medical intermediates at a high yield. Therefore, this coupling method is still not desirable as an industrial production method.

CITATION LIST

Patent Literature

[PTL 1]: Japanese Unexamined Patent Publication No. 2006-231318
[PTL 2]: Japanese Unexamined Patent Publication No. 1992-173756
[PTL 3]: Japanese Unexamined Patent Publication No. 2000-95713

Non-Patent Literature

[NPL 1]: Chemical Reviews, 1995, Volume 95, p 2457-2483
[NPL 2]: Journal of the American Chemical Society, 1972, Volume 94, p 43747-4376
[NPL 3]: Journal of the American Chemical Society, 2002, Volume 124, p 13856-13863

SUMMARY OF INVENTION

Technical Problem

An object of the present invention is to provide a catalyst that has a significant effect for improving conventional cross-coupling reactions, which are unsatisfactory from an industrial standpoint; and a process for the production of a cross-coupling compound using the catalyst.

Technical Solution

The present inventor found a novel catalyst composition containing an iron or cobalt fluoride, and a nitrogen-containing heterocyclic ring compound having a specific structure. The catalyst composition exhibits significantly high activity in the cross-coupling reaction of an organic magnesium compound and an organic halogen compound.

Based on this finding, the present invention provides the following cross-catalyst composition for use in a cross-coupling reaction, and a production process for a cross-coupling compound.

Solution to Problem

Item 1. A catalyst composition for use in a cross-coupling reaction containing an iron or cobalt fluoride and a nitrogen-containing heterocyclic ring compound represented by General Formula (1A),

[Chem. 1]

(1A)

wherein $R^1$ and $R^2$ are same or different, and represent substituted or unsubstituted aryl group, heteroaryl group, alkyl group, cycloalkyl group, or adamantyl group; $R^3$ and $R^4$ are same or different, and represent hydrogen, substituted or unsubstituted aryl group, heteroaryl group, alkyl group, cycloalkyl group, adamantyl group, alkoxy group, or silyl group having three substituents selected from the group consisting of alkyl groups and aryl groups; and $R^3$ and $R^4$, taken with the carbon atoms to which they are attached, may form a saturated or unsaturated ring structure comprising carbons and/or one or more hetero elements,

[Chem. 2]

represents a single bond or a double bond, and X⁻ represents a monovalent anion.

Item 2. A catalyst composition for use in a cross-coupling reaction containing an iron or cobalt fluoride and a nitrogen-containing heterocyclic ring compound represented by General Formula (1B),

[Chem. 3]

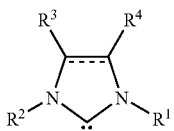

(1B)

wherein $R^1$, $R^2$, $R^3$, $R^4$, and

[Chem. 4]

are as defined above.

Item 3. A method for producing a cross-coupling compound, represented by General Formula (4), $$R^5\text{—}R^6 \quad (4)$$

wherein $R^5$ and $R^6$ each represent substituted or unsubstituted aryl group, substituted or unsubstituted heteroaryl group, or alkyl group, the method comprising the step of:

subjecting an organic magnesium compound represented by General Formula (2), $$R^5\text{—}MgY_1 \quad (2)$$

wherein $R^5$ is as defined above, and $Y_1$ represents halogen; and an organic halogen compound represented by General Formula (3), $$R^6\text{—}Y_2 \quad (3)$$

wherein $R^5$ is as defined above, and $Y_1$ represents halogen or $R^5$, to a cross-coupling reaction in the presence of the catalyst composition according to Item 1 or 2.

Item 4. The method according to Item 3 wherein the cross-coupling reaction is performed by adding a deprotonating agent to a reaction system.

Item 5. The method according to Item 4 wherein the deprotonating agent is an organic metallic compound, metal hydride compound, metal alkoxide or metal amide.

Item 6. The method according to any one of Items 3 to 5, wherein $R^5$ and $R^6$ are different.

Item 7. The method according to any one of Items 3 to 6 wherein the iron or cobalt fluoride is $FeF_2$, $FeF_3$, $FeClF_2$, $FeF_6$, $CoF_2$ or $CoF_3$.

Advantageous Effects of Invention

The production process of the present invention enables conventional, unsatisfactory cross-coupling reactions to be performed more advantageously. Particularly, the method of the present invention enables the production of non-symmetrical biaryl compounds and the like useful for liquid crystalline materials or medical intermediates at a high yield. Further, the novel catalyst composition of the present invention can be produced at low cost, as it does not contain expensive metal elements such as palladium.

The catalyst composition of the present invention is a novel catalyst composition that has not been published before. It is surprising that such a novel catalyst composition exhibits high activity in a cross-coupling reaction.

DESCRIPTION OF EMBODIMENTS

The present invention is more specifically described below.

Catalyst Composition for Use in Cross-Coupling Reaction

The present invention provides a catalyst composition for use in a cross-coupling reaction containing an iron or cobalt fluoride and a nitrogen-containing heterocyclic ring compound (hereinafter, this compound may be simply referred to as a nitrogen-containing heterocyclic ring compound (1)) represented by General Formula (1A),

[Chem. 5]

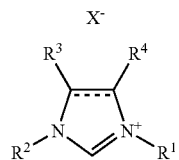

(1A)

wherein $R^1$ and $R^2$ are same or different, and represent substituted or unsubstituted aryl group, heteroaryl group, alkyl group, cycloalkyl group, or adamantyl group; $R^3$ and $R^4$ are same or different, and represent hydrogen, substituted or unsubstituted aryl group, heteroaryl group, alkyl group, cycloalkyl group, adamantyl group, alkoxy group, or silyl group having three substituents selected from the group consisting of alkyl groups and aryl groups; and $R^3$ and $R^4$, taken with the carbon atoms to which they are attached, may form a saturated or unsaturated ring structure comprising carbons and/or one or more hetero elements,

[Chem. 6]

represents a single bond or a double bond, X⁻ represents a monovalent anion, or by General Formula (1B),

[Chem. 7]

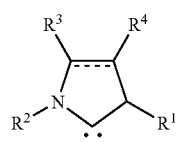

(1B)

wherein $R^1$, $R^2$, $R^3$ and $R^4$ and

[Chem. 8]

----- are as defined above.

Examples of iron fluorides include $FeF_2$, $FeF_3$, $FeClF_2$ and $FeF_6$. The oxidation number of the iron is generally 2 or 3. The iron fluoride can be produced by mixing a iron chloride with another fluoride material, and generating an iron fluoride ($FeF_2$, $FeF_3$, $FeClF_2$, $FeF_6$ and the like) in a reaction system.

Examples of cobalt fluorides include $CoF_2$, $CoF_3$, $CoClF_2$ and $CoF_6$. The oxidation number of the cobalt is generally 2 or 3.

The iron or cobalt fluorides may be metal salts obtained by mixing iron or cobalt chloride, bromide, or iodide with a metal fluoride such as potassium fluoride, or sodium fluoride. The iron or cobalt fluoride may be an anhydride, hydrate or solvate.

The iron and cobalt fluorides may be used singly or in a combination of two or more kinds.

The iron and cobalt fluorides are preferably hydrates that have a higher solubility in the solvent.

The proportion of iron and/or cobalt fluoride to the N-heterocyclic compound represented by General Formula (1A) is 1 to 99 parts by weight, preferably 5 to 50 parts by weight, more preferably 10 to 35 parts by weight, based on the sum of the parts by weight (100 parts by weight) of the iron and/or cobalt fluoride and N-heterocyclic compound.

In General Formulae (1A) and (1B), the aryl groups represented by $R^1$, $R^2$, $R^3$ or $R^4$ may be a C5-18 aryl, such as phenyl, naphthyl, biphenyl, anthracenyl or terphenyl.

Each aryl group represented by $R^1$, $R^2$, $R^3$ or $R^4$ may contain 1 to 9, 1 to 5, particularly 1 to 3 substituents.

Examples of the substituents contained in the aryl groups represented by $R^1$, $R^2$, $R^3$ and $R^4$ include a silyl group having three substituents selected from the group consisting of C1-12 alkyl or aryl groups, C1-12 alkoxy groups, and C6-12 aryloxy groups.

Examples of the C1-12 alkyl groups include straight-chain or branched-chain C1-12 alkyl groups, such as methyl, ethyl, propyl, isopropyl, butyl, isobutyl, t-butyl, pentyl, hexyl, octyl, decyl, and dodecyl groups.

Examples of the silyl groups having the three substituents selected from the group consisting of alkyl or aryl groups include silyl groups having three substituents (same or different) selected from the group consisting of C1-6 (preferably 1 to 4) alkyl groups and the above-mentioned aryl groups; namely, trimethylsilyl, triethylsilyl, t-butyldimethylsilyl, triphenylsilyl, or triisopropylsilyl group.

Examples of C1-6 alkyl groups include straight-chain or branched-chain C1-6 alkyl groups, such as methyl, ethyl, propyl, isopropyl, butyl, isobutyl, t-butyl, pentyl, or hexyl.

Examples of the C1-12 alkoxy groups include an alkoxy having an alkyl moiety of one of the above-mentioned C1-12 (preferably 1 to 6) alkyl groups; namely, straight-chain or branched-chain C1-12 alkoxy group such as methoxy, ethoxy, isopropoxy, or t-butoxy. Examples of the C6-12 aryloxy groups include phenoxy, benzyloxy, and 2,4,6-trimethylphenoxy groups.

Therefore, examples of the aryl groups, represented by $R^1$, $R^2$, $R^3$ and $R^4$ in General Formulae (1A) and (1B) that may contain substituents, include phenyl, naphthyl, biphenyl, anthracenyl, terphenyl, 2,4,6-trimethylphenyl, 2,6-diisopropylphenyl, 2,6-dimethoxyphenyl, and 2,4,6-trimethylsilylphenyl groups.

Examples of heteroaryl groups represented by $R^1$, $R^2$, $R^3$ and $R^4$ in General Formulae (1A) and (1B) include a 5- to 6-membered ring heteroaryl containing at least one (preferably 1 to 4) heteroatoms selected from the group consisting of nitrogen, oxygen and sulfur; namely, furyl, thienyl, pyridyl, or pyrimidyl.

Examples of alkyl groups represented by $R^1$, $R^2$, $R^3$ and $R^4$ in General Formulae (1A) and (1B) include the above-mentioned C1-12 alkyl groups (preferably C1-8 alkyl groups); namely, straight-chain or branched-chain C1-12 alkyl groups such as methyl, ethyl, propyl, isopropyl, butyl, isobutyl, t-butyl, pentyl, hexyl, octyl, decyl, or dodecyl groups.

Examples of cycloalkyl groups represented by $R^1$, $R^2$, $R^3$ and $R^4$ in General Formulae (1A) and (1B) include the C3-12 (preferably C5-7) cycloalkyl groups; namely, cyclopropyl, cyclobutyl, cyclopentyl, cyclohexyl, cyclooctyl, cyclodecyl, or cyclododecyl groups.

Examples of alkoxy groups represented by $R^3$ and $R^4$ in General Formulae (1A) and (1B) include the above-mentioned C1-12 alkoxy groups.

Examples of the silyl groups, represented by $R^3$ and $R^4$ in General Formulae (1A) and (1B), which have the three substituents selected from the group consisting of alkyl or aryl groups, include silyl groups having three substituents selected from the group consisting of the above-mentioned alkyl or aryl groups.

Examples of the "saturated or unsaturated cyclic structure formed of a carbon or a hetero element" formed by $R^3$ and $R^4$, taken together with the carbon atoms to which they are attached, include benzene, thiophene, furan, pyrrole, cyclohexane, imidazole, pyran, pyridine, pyrimidine, pyrazine, pyridazine, thiazole, oxazole, isooxazole, thiadiazole, pyrrolidine, pyrazoline, imidazoline, piperidine, piperazine, and morpholine.

Examples of the monovalent anions represented by $X^-$ include $F^-$, $Cl^-$, $Br^-$, $I^-$, $[OSO_2CH_3]^-$, $[OSO_2CF_3]^-$, $[OSO_2C_6H_4CH_3]^-$, $[N(SO_2CF_3)_2]^-$, $[N(SO_2C_6H_4CH_3)_2]^-$, $[N(SO_2CH_3)_2]^-$, $BF_4^-$, $BAr_4^-$, $PF_6^-$, $AsF_6^-$, $SbF_6^-$, $C_6F_5^-$, $ClO_4^-$, and alkoxides such as methoxide, ethoxide, t-butoxide, or phenoxide.

Examples of the nitrogen-containing heterocyclic ring compounds represented by General Formula (1A) or General Formula (1B) include 1,3-bis(2,6-diisopropylphenyl)imidazolinium chloride, 1,3-bis(2,6-diisopropylphenyl)imidazolinium tetrafluoroborate, 1,3-bis(2,6-diisopropylphenyl)imidazolidin-2-ylidene, 1,3-bis(2,6-diisopropylphenyl)imidazolium chloride, 1,3-bis(2,6-diisopropylphenyl)imidazolium tetrafluoroborate, 1,3-bis(2,6-diisopropylphenyl)imidazol-2-ylidene, 1,3-bis(2,4,6-trimethylphenyl)imidazolinium chloride, 1,3-bis(2,4,6-trimethylphenyl)imidazolinium tetrafluoroborate, 1,3-bis(2,4,6-trimethylphenyl)imidazolidin-2-ylidene, 1,3-bis(2,4,6-trimethylphenyl)imidazolium chloride, 1,3-bis(2,4,6-trimethylphenyl)imidazolium tetrafluoroborate, 1,3-bis(2,4,6-trimethylphenyl)imidazol-2-ylidene, 1,3-di-tert-butylimidazolinium chloride, 1,3-di-tert-butylimidazolinium tetrafluoroborate, 1,3-di-tert-butylimidazolidin-2-ylidene, 1,3-di-tert-butylimidazolium chloride, 1,3-di-tert-butylimidazolium tetrafluoroborate, 1,3-di-tert-butylimidazol-2-ylidene, 1,3-bis(1-adamantyl)imidazolinium tetrafluoroborate, 1,3-bis(1-adamantyl)imidazolium tetrafluoroborate, and 1,3-bis(1-adamantyl)benzimidazolinium tetrafluoroborate.

Particularly preferred among the above-mentioned compounds is a nitrogen-containing heterocyclic ring compound in which $R^1$ and $R^2$ represent an aryl group (preferably phenyl group) having 1 to 3 substituents (preferably C1-6 alkyl group), or an alkyl group (preferably C1-6 alkyl group), and in which $R^3$ and $R^4$ represent a hydrogen.

The nitrogen-containing heterocyclic ring compounds are known compounds, and can be easily produced by known methods.

Further, the proportion of the nitrogen-containing heterocyclic ring compound is generally about 1 to 5 mol, preferably 1 to 3 mol, per mol of the iron or cobalt fluoride.

Where $Y_1$ is $R^5$, the compound of General Formula (2) represents an organic magnesium compound having a composition: $R^5_2Mg$.

The catalyst composition for use in the cross-coupling reaction of the present invention may be a compound in which the iron and/or cobalt fluoride and the nitrogen-containing heterocyclic ring compound exist separately, or a compound in which at least a part of these compounds is complexed, as above.

Further, the catalyst composition for use in the cross-coupling reaction of the present invention may be formed only of the iron and/or cobalt fluoride and the nitrogen-containing heterocyclic ring compound, or may further contain an organic phosphorous compound.

Examples of the organic phosphorous compound include phosphine and phosphite.

Examples of the phosphine include triphenylphosphine, trimethylphosphine, tricyclohexylphosphine, tri-t-butylphosphine, bisdiphenylphosphinoethane, and bisdiphenylphosphinopropane.

Examples of the phosphite include trimethoxyphosphite, triethoxyphosphite, and triphenoxyphosphite.

The proportion of the nitrogen-containing heterocyclic ring compound is generally about 1 to 5 mol, preferably 2 to 3 mol, per mol of the organic phosphorous compound.

The catalyst composition for use in cross-coupling reaction of the present invention arbitrarily contains an amine compound (pyridine, triethylamine, N,N,N',N'-tetramethylethylenediamine and the like), representative metal halide (zinc chloride, zinc bromide, sodium iodide and the like), unsaturated carbon hydride (ethylene, styrene, butadiene, cyclooctadiene, norbornadiene, diphenylacetylene and the like).

When the catalyst composition for use in the cross-coupling reaction of the present invention contains those arbitrary ingredients, the contents of the iron or cobalt fluoride and the nitrogen-containing heterocyclic ring compound in the composition are adjusted, for example, in a range of 1 to 99% by weight.

Production Process for Cross-Coupling Compound

The present invention provides a method for producing a cross-coupling compound, represented by General Formula (4),

$$R^5-R^6 \quad (4)$$

wherein $R^5$ and $R^6$ each represent substituted or unsubstituted aryl group, substituted or unsubstituted heteroaryl group, or alkyl group, the method comprising the step of:
subjecting an organic magnesium compound represented by General Formula (2),

$$R^5-MgY_1 \quad (2)$$

wherein $R^5$ is as defined above, and $Y_1$ represents halogen or $R^5$; and
an organic halogen compound represented by General Formula (3),

$$R^6-Y_2 \quad (3)$$

wherein $R^6$ is as defined above, and $Y_2$ represents halogen, to a cross-coupling reaction in the presence of the above-mentioned catalyst composition for use in cross-coupling reaction.

Examples of the aryl groups represented by $R^5$ include C5-12 aryl groups, such as cyclopentadienyl, phenyl, naphthyl, or biphenyl.

The aryl group represented by $R^5$ may contain 1 to 6 (preferably 1 to 3) substituents.

Examples of the substituents contained in the aryl group represented by $R^5$ include the above-mentioned C1-12 alkyl groups, the above-mentioned C1-12 alkoxy groups, the above-mentioned cycloalkyl groups, adamantyl groups, and halogens.

Examples of the halogens include fluorine, chlorine, bromine, and iodine.

Examples of the heteroaryl groups represented by $R^5$ include 5 to 12-membered ring heteroaryls containing at least 1 (preferably 1 to 4) heteroatom selected from the group consisting of nitrogen, oxygen and sulfur; namely, thienyl, furyl, pyridyl, pyrimidinyl, phenanthrolinyl, pyrrolyl, isooxazolyl, isothiazolyl, oxazolyl, thiazolyl, imidazolyl, quinolinyl, isoquinolinyl, naphthyridinyl, and indolyl.

The heteroaryl group represented by $R^5$ may contain 1 to 6 (preferably 1 to 3) substituents.

Examples of the substituents contained in the heteroaryl group represented by $R^5$ include the above-mentioned C1-12 alkyl groups, the above-mentioned C1-12 alkoxy groups, the above-mentioned cycloalkyl groups, adamantyl groups, and the above-mentioned halogens.

Examples of alkyl group represented by $R^5$ include the above-mentioned C1-12 alkyl groups.

Examples of the halogens represented by $Y^1$ include fluorine, chlorine, bromine, and iodine. Particularly preferred is bromine.

Particularly preferred among the organic magnesium compound (2) is, for example, an organic magnesium compound (2) in which $R^5$ contains 1 to 3 substituents (preferably C1-12 (preferably C1-6) alkyl groups, halogens, or C1-12 (preferably C1-6) alkoxy groups) or unsubstituted aryl groups (preferably phenyl groups or naphthyl groups); or heteroaryl groups (preferably thienyl group) or C1-12 (preferably C1-6) alkyl groups.

These organic magnesium compounds (2) are known compounds, and can be easily produced by known methods.

Examples of the aryl groups represented by $R^6$ include C5-18 aryl groups such as cyclopentadienyl, phenyl, naphthyl, biphenyl, or anthracenyl.

The aryl groups represented by $R^6$ may contain 1 to 10 (preferably 1 to 5) substituents.

Examples of the substituents contained in the aryl groups represented by $R^6$ include the above-mentioned C1-12 alkyl groups; the above-mentioned C1-12 alkoxy groups; amino groups having 1 or 2 substituents selected from the group consisting of alkyl, aryl and arylalkyl; the above-mentioned halogens; C1-12 alkylthio groups; and dioxolanyl groups.

Examples of the amino groups having 1 or 2 substituents selected from the group consisting of alkyl, aryl and arylalkyl include amino groups selected from the group consisting of the above-mentioned C1-12 alkyl groups; the above-mentioned C5-12 aryl groups; and the above-mentioned C1-12 alkyl groups substituted with 1 to 3 C5-12 aryl groups; namely, methylamino, dimethylamino, ethylamino, diethylamino, n-propylamino, isopropylamino, n-butylamino, sec-butylamino, tert-butylamino, isobutylamino, n-pentylamino, isopentylamino, neopentylamino, 1-ethylpropylamino, n-hexylamino, 1,2,2-trimethylpropylamino, 2-ethylbutylamino, 3,3-dimethylbutylamino, isohexylamino, 3-methylpentylamino, phenylamino, benzylamino, diphenylamino, dibenzylamino group and the like.

Examples of the C1-12 alkylthio groups include alkylthio groups having an alkyl moiety of the above-mentioned straight-chain or branched-chain C1-12 alkyl group.

Examples of the heteroaryl groups represented by $R^6$ include 5- to 14-membered ring heteroaryls having at least 1 (preferably 1 to 4) heteroatoms selected from the group consisting of nitrogen, oxygen and sulfur; namely, thienyl, pyridyl, quinolyl, 2-phenylpyridyl, phenanthrolinyl, terpyridyl, pyrrolyl, isooxazolyl, isothiazolyl, oxazolyl, thiazolyl, imidazolyl, quinolinyl, isoquinolinyl, naphthyridinyl, indolyl and the like.

The heteroaryl groups represented by $R^6$ may contain 1 to 10 (preferably 1 to 5) substituents.

Examples of the substituents contained in the heteroaryl groups represented by $R^6$ are the same as those for the substituents contained in the aryl groups represented by $R^6$.

Examples of the alkenyl groups represented by $R^6$ include straight-chain or branched-chain C2-8 (preferably C2-4) alkenyl groups containing 1 to 3 double bonds, including both trans isomers and cis isomers. More specifically, the examples include vinyl, 1-propenyl, 2-propenyl, 1-methyl-1-propenyl, 2-methyl-1-propenyl, 2-methyl-2-propenyl, 1-butenyl, 2-butenyl, 3-butenyl, 2-pentenyl, 1-pentenyl, 3-pentenyl, 4-pentenyl, 1,3-butadienyl, 1,3-pentadienyl, 2-penten-4-yl, 1-hexenyl, 2-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, 1,4-hexadienyl, α-styryl, and β-styryl group.

Examples of the halogens represented by $Y^2$ include fluorine, chlorine, bromine, iodine and the like. Chlorine and bromine are particularly preferable.

Particularly preferred among the above-mentioned organic halogen compounds (3) is an organic halogen compound (3) in which $R^6$ contains 1 to 3 substituents (preferably C1-12 (preferably C1-6) alkyl groups, C1-12 (preferably C1-6) alkoxy groups, an amino group containing 1 to 2 C1-12 (preferably C1-6) alkyl groups, halogens, C1-12 (preferably C1-6) alkylthio groups, or dioxolanyl groups), or an organic halogen compound (3) in which $R^6$ represents unsubstituted aryl groups (preferably phenyl group); or heteroaryl groups (preferably pyridyl group).

These organic halogen compounds (3) are known compounds, and can be easily produced by known methods.

In the method of the present invention, the proportion of the organic halogen compound (3) in the catalyst composition of the present invention is generally about 0.01 to 0.20 mol, preferably 0.02 to 0.10 mol, per mol of the iron or cobalt fluoride.

In the method of the present invention, when using a catalyst composition for a coupling reaction containing the nitrogen-containing heterocyclic ring compound (1B) represented by General Formula (1B), which is a carbene compound (hereinafter, this compound may be simply referred to as a nitrogen-containing heterocyclic ring compound (1B)), the nitrogen-containing heterocyclic ring compound (1B) is complexed with the iron or cobalt fluoride to serve as a catalyst.

In the embodiments, the proportion of the organic magnesium compound (2) is generally about 1 to 3 equivalent, preferably 1.1 to 1.5 equivalent of the organic halogen compound (3).

In the method of the present invention, when using a catalyst composition for a coupling reaction containing a nitrogen-containing heterocyclic ring compound represented by General Formula (1A) (hereinafter, this compound may be simply referred to as a nitrogen-containing heterocyclic ring compound (1A)), the nitrogen-containing heterocyclic ring compound (1A) is deprotonated by the organic magnesium compound (2) to be a nitrogen-containing heterocyclic ring compound (1B), forming a complex with the iron or cobalt fluoride.

Therefore, when using the nitrogen-containing heterocyclic ring compound (1A) as the nitrogen-containing heterocyclic ring compound, the amount of the organic magnesium compound (2) to be added to the reaction system must be the sum of the amount as a raw material compound to be coupled with a halogenated aromatic compound and the amount required for the deprotonation of the nitrogen-containing heterocyclic ring compound (1A).

In the embodiment, the proportion of the organic magnesium compound (2) is generally about 1 to 3 equivalent, preferably 1.1 to 2.0 equivalent of the organic halogen compound (3).

In the method of the present invention, the previously prepared catalyst composition may be added to the reaction system, or the nitrogen-containing heterocyclic ring compound (1) and the iron or cobalt fluoride (and phosphorus compound and the like, as required) may be mixed inside the reaction system.

Therefore, the present invention does not particularly specify the order of the addition of the iron or cobalt fluoride; nitrogen-containing heterocyclic ring compound; organic halogen compound (3); and organic magnesium compound (2). These compounds may all be mixed at once, or two or three of them may be mixed first before the rest is added thereto.

Though it depends on the kind of the solvent or other conditions, the cross-coupling reaction of the present invention is generally carried out at 0 to 150° C., preferably 60 to 120° C., for 6 to 48 hours, preferably 12 to 36 hours, under argon or nitrogen atmosphere.

In a preferred embodiment of the method of the present invention, the reaction system may contain a deprotonating agent.

By previously deprotonating the nitrogen-containing heterocyclic ring compound (1A) and iron or cobalt fluoride hydrate using the deprotonating agent, a smaller amount of the organic magnesium compound (2) is consumed during the deprotonation of the nitrogen-containing heterocyclic ring compound (1A) and/or the iron or cobalt fluoride hydrate. Therefore, it is possible to reduce the amount of the organic magnesium compound (2).

In the embodiment, the proportion of the organic magnesium compound (2) is generally about 1 to 3 equivalent, preferably 1.1 to 1.5 equivalent of the organic halogen compound (3).

When using a deprotonating agent, the reagent can be added at any time, as long as the nitrogen-containing heterocyclic ring compound (1A) and the deprotonating agent are supplied to the reaction system before the organic magnesium compound (2) is added to previously complete the deprotonation of the nitrogen-containing heterocyclic ring compound (1A).

The deprotonating agent is not limited, as long as it is capable of deprotonating the nitrogen-containing heterocyclic ring compound (1A). Examples of the deprotonating agents include organic metal compounds such as Grignard reagent or alkyl lithium; metal hydride compounds; metal alkoxides; and metal amides.

Examples of the Grignard reagent include methylmagnesium halides, ethylmagnesium halides, and phenylmagnesium halides.

Examples of the alkyl lithium include methyllithium and n-butyllithium.

Examples of the metal hydride compounds include NaH and KH.

Examples of the metal alkoxides include sodium methoxido, sodium ethoxide, and potassium t-butoxide.

Examples of the metal amides include lithium amide, sodium amide, and potassium amide.

The proportion of the deprotonating agent is generally about 1 to 2 mol, preferably 1 to 1.2 mol, per mol of the nitrogen-containing heterocyclic ring compound (1A).

The proportion of the deprotonating agent is generally about 1 to 1.5 mol, preferably 1 to 1.2 mol, per mol of the water molecules contained in the iron or cobalt fluoride hydrate.

When using Grignard reagent as a deprotonating agent, if the amount exceeds the above range, the deprotonating agent is reacted with the organic halogen compound (3), thereby producing a by-product.

The deprotonation of the nitrogen-containing heterocyclic ring compound (1A) and the iron or cobalt fluoride hydrate by the deprotonating agent is carried out at generally 0 to 60° C., preferably 0 to 30° C., for 1 to 48 hours, preferably for 3 to 12 hours.

The reaction of the present invention is generally carried out in an usual solvent that does not cause any adverse effects during the reaction, such as tetrahydrofuran (THF), diethyl ether, tetrahydropyran (THP), 1,4-dioxane, dibutyl ether, methylcyclohexyl ether, 1,2-dimethoxyethane and like ether-based solvents; N,N-dimethylformamide, N,N-dimethylacetoamide, dimethylsulfoxide, N-methylpiperazine (NMP), hexamethylphosphorylamide (HMPA) and like aprotic polar solvents; methylene chloride, ethylene chloride, 1,2-dichlorobenzene and like halogenated hydrocarbon-based solvent; benzene, toluene, xylene mesitylene and like aromatic solvents, or other organic solvents.

The cross-coupling compound, which is the target product of the reaction mixture, is easily separated and purified by usual separation means and purification means such as various chromatographies, distillation, or recrystallization.

The separation and purification is preferably carried out using a composition for use in a cross-coupling reaction that does not contain an organic phosphorous compound, such as a phosphine compound, so as to more easily perform the separation and purification of the cross-coupling compound.

EXAMPLES

Hereinafter, the present invention will be described in more detail with reference to the Examples.

Example 1

Preparation of 4-methylbiphenyl

A THF solution of ethylmagnesium bromide (0.167 mL, 1.08 M, 0.18 mmol) was added to $FeF_3 \cdot 3H_2O$ (5.01 mg, 0.03 mmol) and 1,3-bis(2,6-diisopropylphenyl)imidazolinium chloride (38.4 mg, 0.09 mmol) at 0° C. under argon atmosphere. The following process was also performed under argon atmosphere. THF (0.10 mL) was added to rinse the internal wall of the reaction vessel. After stirring for five hours at room temperature, chlorobenzene (112.6 mg, 1.0 mmol) and a THF solution (1.18 mL, 1.02 M, 1.2 mmol) of p-tolylmagnesium bromide was added to the mixture at 0° C., and the mixture was reacted for 24 hours at 60° C. After cooled to the ambient temperature, 2.0 mL of saturated sodium potassium tartrate aqueous solution was added to the reaction mixture. The water layer was extracted five times using $Et_2O$. The total organic extract was filtrated by Florisil pad (100-200 mesh, Nacalai Tesque, Inc.). As the internal standard, gas chromatographic analysis was performed using undecane (42.2 µL, 0.2 mmol) (yield=98%). After removing the solvent under reduced pressure, the crude product was purified by silica gel chromatography (pentane), thereby obtaining the above compound, which was a colorless liquid (0.163 g, yield=97%, purity=>99% (GC analysis)).

Example 2

Preparation of 2-methoxy-2'-methylbiphenyl

A THF solution of ethylmagnesium bromide (0.167 mL, 1.08 M, 0.18 mmol) was added to $FeF_3 \cdot 3H_2O$ (5.01 mg, 0.03 mmol) and 1,3-bis(2,6-diisopropylphenyl)imidazolinium chloride (38.4 mg, 0.09 mmol) at 0° C. under argon atmosphere. The following process was also performed under argon atmosphere. THF (0.10 mL) was added to rinse the internal wall of the reaction vessel. After stirring for five hours at room temperature, 1-methoxy-2-chlorobenzene (142.6 mg, 1.0 mmol) and a THF solution (1.50 mL, 0.80 M, 1.2 mmol) of o-tolylmagnesium bromide was added to the mixture at 0° C., and the mixture was reacted for 24 hours at 80° C. After cooled to the ambient temperature, 2.0 mL of saturated sodium potassium tartrate aqueous solution was added to the reaction mixture. The water layer was extracted five times using $Et_2O$. The total organic extract was filtrated by Florisil pad (100-200 mesh, Nacalai Tesque, Inc.). After removing the solvent under reduced pressure, the crude product was purified by silica gel chromatography (toluene=15, 30 and 50% in hexane), thereby obtaining the above compound, which was a colorless liquid (0.178 g, yield=90%, purity=>99% (GC analysis)).

Example 3

Preparation of 4-methoxy-4'-methylbiphenyl

Using a THF solution of p-tolylmagnesium bromide (1.18 mL, 1.02 M, 1.2 mmol) and 1-methoxy-4-chlorobenzene (142.6 mg, 1.0 mmol) as starting materials, the reaction was performed at a scale of 1.0 mmol at 60° C. for 24 hours in the same manner as in Example 2. After performing silica gel column chromatography (toluene=15, 30 and 50% in hexane), the above compound was obtained as a white solid (0.182 g, yield=92%, purity=>99% (GC analysis)).

Example 4

Preparation of 4-butyl-4'-fluorobiphenyl

Using a THF solution of 4-fluorophenylmagnesium bromide (1.46 mL, 1.03 M, 1.5 mmol), 4-butylchlorobenzene (168.7 mg, 1.0 mmol), $FeF_3 \cdot 3H_2O$ (6.68 mg, 0.04 mmol) and 1,3-bis(2,6-diisopropylphenyl)imidazolinium chloride (51.2 mg, 0.12 mmol) as starting materials, the reaction was performed at a scale of 1.0 mmol at 60° C. for 24 hours in the same manner as in Example 2. After performing silica gel column chromatography (pentane), the above compound was obtained as a white solid (0.199 g, yield=87%, purity=>97% (GC analysis)).

Example 5

Preparation of biphenyl-3-yl-dimethylamine

Using a THF solution of phenylmagnesium bromide (1.19 mL, 1.01 M, 1.2 mmol) and 3-chloro-N,N-dimethylaniline (155.6 mg, 1.0 mmol) as starting materials, the reaction was performed at a scale of 1.0 mmol at 60° C. for 24 hours in the same manner as in Example 2. After performing silica gel column chromatography (toluene=50 and 100% in hexane), the above compound was obtained as a colorless liquid (0.185 g, yield=94%, purity=>98% (GC analysis)).

Example 6

Preparation of 4-fluoro-4'-methoxybiphenyl

Using a THF solution of p-methoxyphenylmagnesium bromide (1.88 mL, 0.64 M, 1.2 mmol) and 1-chloro-4-fluorobenzene (130.6 mg, 1.0 mmol) as starting materials, the reaction was performed at a scale of 1.0 mmol at 60° C. for 24 hours in the same manner as in Example 2. After performing silica gel column chromatography (toluene=15, 30 and 50% in hexane), the above compound (0.184 g, yield=91%, purity=>99% (GC analysis)) was obtained as a white solid.

Example 7

Preparation of 1-(2-methoxyphenyl) naphthalene

Using a THF solution of 1-naphthylmagnesium bromide (4.62 mL, 0.26 M, 1.2 mmol), 1-chloro-2-methoxybenzene (142.6 mg, 1.0 mmol), $FeF_3 \cdot 3H_2O$ (8.34 mg, 0.05 mmol) and 1,3-bis(2,6-diisopropylphenyl)imidazolinium chloride (64.1 mg, 0.15 mmol) as starting materials, the reaction was performed at a scale of 1.0 mmol at 70° C. for 48 hours in the same manner as in Example 2. After performing silica gel column chromatography (toluene=10, 20 and 40% in hexane), the above compound was obtained as a white solid (0.215 g, yield=92%, purity=>99% (GC analysis)).

Example 8

Preparation of 2-(2-methoxyphenyl)naphthalene

Using a THF solution of 2-naphthylmagnesium bromide (1.47 mL, 1.02 M, 1.5 mmol), and 1-chloro-2-methoxybenzene (142.6 mg, 1.0 mmol) as starting materials, the reaction was performed at a scale of 1.0 mmol at 70° C. for 48 hours in the same manner as in Example 2. After performing silica gel column chromatography (toluene=10, 20 and 40% in hexane), the above compound was obtained as a white solid (0.224 g, yield=96%, purity=>99% (GC analysis)).

Example 9

Preparation of 2-(biphenyl-4-yl)-[1,3]-dioxolan

Using a THF solution of phenylmagnesium bromide (1.34 mL, 1.01 M, 1.35 mmol) and 2-chlorophenyl-[1,3]-dioxolan (184.6 mg, 1.0 mmol) as starting material, the reaction was performed at a scale of 1.0 mmol at 70° C. for 48 hours in the same manner as in Example 2. After performing silica gel column chromatography (diethylether=5, 10 and 20% in hexane), the above compound was obtained as a white solid (0.199 g, yield=88%, purity=>99% (GC analysis)).

Example 10

Preparation of 3,4-difluoro-4'-methoxybiphenyl

Using a THF solution of p-methoxyphenylmagnesium bromide (2.34 mL, 0.64 M, 1.5 mmol), 4-chloro-1,2-difluorobenzene (148.6 mg, 1.0 mmol), $FeF_3 \cdot 3H_2O$ (8.34 mg, 0.05 mmol) and 1,3-bis(2,6-diisopropylphenyl)imidazolinium chloride (64.1 mg, 0.15 mmol) as starting materials, the reaction was performed at a scale of 1.0 mmol at 60° C. for 24 hours, and then at 80° C. for 12 hours, in the same manner as in Example 2. After performing silica gel column chromatography (toluene=15, 30 and 50% in hexane), the above compound was obtained as a white solid (0.215 g, yield=92%, purity=>99% (GC analysis)).

Example 11

Preparation of 2-(2,4,6-trimethylphenyl)-pyridine

Using a THF solution of mesitylmagnesium bromide (0.974 mL, 0.77 M, 0.75 mmol), 2-bromopyridine (158.0 mg, 1.0 mmol), $FeF_3 \cdot 3H_2O$ (5.01 mg, 0.03 mmol) and 1,3-bis(2,6-diisopropylphenyl)imidazolinium chloride (38.4 mg, 0.09 mmol) as starting materials, the reaction was performed at a scale of 1.0 mmol at 90° C. for 24 hours in the same manner as in Example 2. After performing silica gel column chromatography (EtOAc=10 and 20% in hexane), the above compound was obtained as a yellow liquid (0.150 g, yield=76%, purity=>99% (GC analysis)).

Example 12

Preparation of 2-(thienyl-2-yl)-pyridine

Using a THF solution of 2-thienylmagnesium bromide (1.50 mL, 1.00 M, 1.5 mmol), 2-bromopyridine (79.0 mg, 0.5 mmol), $FeF_3 \cdot 3H_2O$ (5.01 mg, 0.03 mmol), and 1,3-bis(2,6-diisopropylphenyl)imidazolinium chloride (38.4 mg, 0.09 mmol) as starting materials, the reaction was performed at a scale of 0.5 mmol at 80° C. for 24 hours in the same manner as in Example 2. After performing silica gel column chromatography (EtOAc=10 and 20% in hexane), the above compound was obtained as a yellow liquid (0.060 g, yield=74%, purity=>99% (GC analysis)).

Example 13

Preparation of 2,4,6-trimethyl Biphenyl

A THF solution of ethylmagnesium bromide (0.167 mL, 1.08 M, 0.18 mmol) was added to $FeF_3 \cdot 3H_2O$ (5.01 mg, 0.03 mmol) and 1,3-bis(2,6-diisopropyl phenyl)imidazolinium chloride (38.4 mg, 0.09 mmol) at 0° C. under argon atmosphere. The following process was also performed under argon atmosphere.

THF (0.10 mL) was added to rinse the internal wall of the reaction vessel. After 10 hours, a THF solution of mesitylmagnesium bromide (1.02 mL, 1.18 M, 1.2 mmol) was added to the mixture at 0° C., and the solvent was removed under reduced pressure. The obtained viscous liquid was dissolved in toluene (1.0 ml), and chlorobenzene (112.6 mg, 1.0 mmol) was added at 0° C. The reaction was performed at 120° C. for 24 hours. After cooled to the ambient temperature, 2.0 mL of saturated sodium potassium tartrate aqueous solution was added to the reaction mixture. The water layer was extracted five times using $Et_2O$. The total organic extract was filtrated

Example 14

Preparation of 1-ethyl-2-methoxybenzene

A THF solution of ethylmagnesium bromide (1.39 mL, 1.08 M, 1.5 mmol) was added to $FeF_3.3H_2O$ (5.01 mg, 0.03 mmol), 1,3-bis(2,6-diisopropylphenyl)imidazolinium chloride (38.4 mg, 0.09 mmol) and 1-chloro-2-methoxybenzene (142.6 mg, 1.0 mmol) at 0° C. under argon atmosphere. The mixture was reacted at 60° C. for 24 hours. After cooled to the ambient temperature, 2.0 mL of saturated sodium potassium tartrate aqueous solution was added to the reaction mixture. The water layer was extracted five times using $Et_2O$. The total organic extract was filtrated by Florisil pad (100-200 mesh, Nacalai Tesque, Inc.). As the internal standard, gas chromatography analysis was performed using undecane (42.2 μL, 0.2 mmol) (yield=94%). After removing the solvent under reduced pressure, the crude product was purified by silica gel chromatography (diethylether=2 and 5% in pentane), thereby obtaining the above compound, which was a colorless liquid (0.120 g, yield=88%, purity=>99% (GC analysis)).

Example 15

Preparation of 2-methoxy-2'-methylbiphenyl

A THF solution of ethylmagnesium bromide (0.324 mL, 1.08 M, 0.35 mmol) was added to $FeF_3.3H_2O$ (8.34 mg, 0.05 mmol) and 1,3-bis(2,6-diisopropylphenyl)imidazolinium chloride (63.8 mg, 0.15 mmol) and triphenylphosphine (13.1 mg, 0.05 mmol) at 0° C. under argon atmosphere. The following process was also performed under argon atmosphere. After stirring for six hours at room temperature, 1-chloro-2-methoxybenzene (142.6 mg, 1.0 mmol) and a THF solution of o-tolylmagnesium bromide (1.88 mL, 0.80 M, 1.5 mmol) was added to the mixture. The mixture was reacted at 60° C. for 24 hours, and then at 80° C. for 12 hours. After cooled to the ambient temperature, 2.0 mL of saturated sodium potassium tartrate aqueous solution was added to the reaction mixture. The water layer was extracted five times using $Et_2O$. The total organic extract was filtrated by Florisil pad (100-200 mesh, Nacalai Tesque, Inc.). After removing the solvent under reduced pressure, the crude product was dissolved in $CH_2Cl_2$ (1.0 mL). Then, m-chloroperbenzoic acid (MCPBA) (0.06 mmol) was added at room temperature, and the reaction mixture was stirred for 30 minutes. After removing the solvent under reduced pressure, the crude product was purified by silica gel chromatography (toluene=15, 30, 50% in hexane), thereby obtaining the above compound, which was a white solid (0.188 g, yield=95%, purity=>99% (GC analysis)).

Example 16

Preparation of 1-(2-methoxyphenyl)naphthalene

A THF solution of ethylmagnesium bromide (0.324 mL, 1.08 M, 0.35 mmol) was added to $FeF_3.3H_2O$ (8.34 mg, 0.05 mmol), 1,3-bis(2,6-diisopropylphenyl)imidazolinium chloride (63.8 mg, 0.15 mmol) and triphenylphosphine (13.1 mg, 0.05 mmol) at 0° C. under argon atmosphere. The following process was also performed under argon atmosphere. After stirring for six hours at room temperature, 1-chloro-2-methoxybenzene (142.6 mg, 1.0 mmol) and a THF suspension of 1-naphthylmagnesium bromide (2.34 mL, 0.64 M, 1.5 mmol) was added to the mixture. The mixture was reacted at 60° C. for 24 hours and then at 80° C. for 12 hours. After cooled to the ambient temperature, 2.0 mL of saturated sodium potassium tartrate aqueous solution was added to the reaction mixture. The water layer was extracted five times using $Et_2O$. The total organic extract was filtrated by Florisil pad (100-200 mesh, Nacalai Tesque, Inc.). After removing the solvent under reduced pressure, the crude product was dissolved in $CH_2Cl_2$ (1.0 mL). Then, m-chloroperbenzoic acid (MCPBA) (0.06 mmol) was added at room temperature, and the reaction mixture was stirred for 30 minutes. After removing the solvent under reduced pressure, the crude product was purified by silica gel chromatography (toluene=15, 30, 50% in hexane), thereby obtaining the above compound, which was a white solid (0.215 g, yield=92%, purity=>99% (GC analysis)).

Example 17

Preparation of 4-butyl-4'-fluorobiphenyl

Using a THF solution of 4-fluorophenylmagnesium bromide (1.46 mL, 1.03 M, 1.5 mmol), 4-butylchlorobenzene (168.7 mg, 1.0 mmol), $FeF_3.3H_2O$ (8.34 mg, 0.05 mmol), 1,3-bis(2,6-diisopropylphenyl)imidazolinium chloride (63.8 mg, 0.15 mmol) and triphenylphosphine (13.1 mg, 0.05 mmol) as starting materials, the reaction was performed at a scale of 1.0 mmol at 60° C. for 24 hours, then at 80° C. for 12 hours in the same manner as in Example 15. After performing silica gel chromatography (pentane), the above compound was obtained as a white solid (0.201 g, yield=88%, purity=>98% (GC analysis)).

Example 18

Preparation of 2-fluoro-4'-methoxybiphenyl

Using a THF solution of p-methoxyphenylmagnesium bromide (2.34 mL, 0.64 M, 1.5 mmol) and 1-chloro-2-fluorobenzene (130.6 mg, 1.0 mmol) as starting materials, the reaction was performed at a scale of 1.0 mmol at 60° C. for 24 hours, then at 80° C. for 12 hours in the same manner as in Example 15. After performing silica gel column chromatography (toluene=15, 30 and 50% in hexane), the above compound (0.135 g, yield=68%, purity=>97% (GC analysis)) was obtained as a white solid.

Example 19

Preparation of 4'-butyl-3,4-difluorobiphenyl

A THF solution of ethylmagnesium bromide (0.486 mL, 1.08 M, 0.525 mmol) was added to $FeF_3.3H_2O$ (12.51 mg, 0.075 mmol), 1,3-bis(2,6-diisopropylphenyl)imidazolinium chloride (95.7 mg, 0.225 mmol) and triphenylphosphine (19.7 mg, 0.075 mmol) at 0° C. under argon atmosphere. The following process was also performed under argon atmosphere. After stirring for six hours at room temperature, 1-butyl-4-chlorobenzene (84.3 mg, 0.5 mmol) and a THF solution of 3,4-difluorophenylmagnesium bromide (1.53 mL, 0.98 M, 1.5 mmol) was added to the mixture. The mixture was reacted at 60° C. for 24 hours, and then at 80° C. for 12 hours. After cooled to the ambient temperature, 2.0 mL of saturated sodium potassium tartrate aqueous solution was added to the reaction mixture. The water layer was extracted five times using Et$_2$O. The total organic extract was filtrated by Florisil pad (100-200 mesh, Nacalai Tesque, Inc.). As the internal standard, gas chromatographic analysis was performed using undecane (42.2 μL, 0.2 mmol) (yield=84%). After removing the solvent under reduced pressure, the crude product was purified by GPC, thereby obtaining the above compound, which was a colorless liquid (0.095 g, yield=77%, purity=>99% (GC analysis)).

$^1$H NMR δ 0.93 (t, J=7.4 Hz, 3H, CH$_2$CH$_3$), 1.38 (quint, J=7.4 Hz, 2H, CH$_2$CH$_3$), 1.62 (quint, J=7.4 Hz, 2H, CH$_2$CH$_2$CH$_3$), 2.63 (t, J=7.4 Hz, 2H, CH$_2$(CH$_2$)$_2$CH$_3$), 7.11-7.42 (m, 5H, aromatic CH); $^{13}$C NMR δ 13.9, 22.4, 33.6, 35.2, 115.7 (d, $^2J_{C-F}$=17.8 Hz), 117.4 (d, $^2J_{C-F}$=17.8 Hz), 122.7 (dd, $^4J_{C-F}$=3.4, $^3J_{C-F}$=5.4 Hz), 126.7 (2C), 129.0 (2C), 136.4 (d, $^4J_{C-F}$=2.8 Hz), 138.3 (dd, $^4J_{C-F}$=3.9, $^3J_{C-F}$=6.1 Hz), 142.7, 148.3 (dd, $^2J_{C-F}$=12.8 Hz, $^1J_{C-F}$=247.5 Hz), 151.9 (dd, $^2J_{C-F}$=12.8 Hz, $^1J_{C-F}$=247.5 Hz). Anal. calcd for C$_{16}$H$_{16}$F$_2$ C, 78.02; H, 6.55. found C, 78.03; H, 6.62.

Example 20

Preparation of 2-(2,4,6-trimethylphenyl)pyridine

A THF solution of ethylmagnesium bromide (0.162 mL, 1.08 M, 0.175 mmol) was added to FeF$_3$.3H$_2$O (4.17 mg, 0.025 mmol), 1,3-bis(2,6-diisopropylphenyl)imidazolinium chloride (31.9 mg, 0.075 mmol) and triphenylphosphine (15.0 mg, 0.025 mmol) at 0° C. under argon atmosphere. The following process was also performed under argon atmosphere. After stirring for six hours at room temperature, a THF solution of mesitylmagnesium bromide (0.974 mL, 0.77 M, 0.75 mmol) was added to the mixture at room temperature. After removing the solvent under reduced pressure, the obtained viscous liquid was dissolved in toluene (1.0 ml), and 2-bromopyridine (79.0 mg, 0.5 mmol) was added at room temperature. The reaction was performed at 100° C. for 12 hours. After cooled to the ambient temperature, 2.0 mL of saturated sodium potassium tartrate aqueous solution was added to the reaction mixture. The water layer was extracted five times using Et$_2$O. The total organic extract was filtrated by Florisil pad (100-200 mesh, Nacalai Tesque, Inc.). After removing the solvent under reduced pressure, the crude product was purified by silica gel chromatography (EtOAc=10 and 20% in hexane), thereby obtaining the above compound, which was a colorless liquid (0.087 g, yield=90%, purity=>99% (GC analysis)).

Example 21

Preparation of 2-(2,4,6-trimethylphenyl)pyridine

The same method as in Example 20 was performed using 2-chloropyridine (56.8 mg, 0.5 mmol) instead of 2-bromopyridine, thereby obtaining the above compound (0.067 g, yield=70%).

Example 22

Preparation of 4-methylbiphenyl

Chlorobenzene (45.0 mg, 0.4 mmol) and a THF solution of p-tolylmagnesium bromide (0.98 mL, 1.02 M, 1.0 mmol) was added to CoF$_2$.4H$_2$O (3.38 mg, 0.02 mmol), and 1,3-bis(2,6-diisopropylphenyl)imidazolinium chloride (25.6 mg, 0.06 mmol) at 0° C. under argon atmosphere. The mixture was reacted at 60° C. for 24 hours. After cooled to the ambient temperature, 1.0 mL of saturated sodium potassium tartrate aqueous solution was added to the reaction mixture. The water layer was extracted five times using Et$_2$O. The total organic extract was filtrated by Florisil pad (100-200 mesh, Nacalai Tesque, Inc.). As the internal standard, gas chromatographic analysis was performed using undecane (42.2 μL, 0.2 mmol) (yield=91%). After removing the solvent under reduced pressure, the crude product was purified by silica gel chromatography (pentane), thereby obtaining the above compound, which was a colorless liquid (0.059 g, yield=88%, purity=>99% (GC analysis)).

Example 23

Preparation of 3,4-difluoro-4'-methoxybiphenyl

A THF solution of ethylmagnesium bromide (0.55 mL, 1.08 M, 0.60 mmol) was added to CoF$_2$.4H$_2$O (17.0 mg, 0.10 mmol) and 1,3-bis(2,6-diisopropylphenyl)imidazolinium chloride (85.4 mg, 0.20 mmol) at 0° C. under argon atmosphere. The following process was also performed under argon atmosphere. After stirring for four hours at room temperature, 4-chloro-1,2-difluorobenzene (297.0 mg, 2.0 mmol) and a THF solution of p-methoxyphenylmagnesium bromide (3.40 mL, 0.88 M, 3.0 mmol) was added to the mixture. The reaction was performed at 60° C. for 12 hours. After cooled to the ambient temperature, 2.0 mL of saturated ammonium chloride aqueous solution was added to the reaction mixture. The water layer was extracted five times using Et$_2$O. The total organic extract was filtrated by Florisil pad (100-200 mesh, Nacalai Tesque, Inc.). After removing the solvent under reduced pressure, the crude product was purified by silica gel chromatography (toluene=5% in hexane), thereby obtaining the above compound, which was a white solid (0.428 g, yield=97%, purity=>98% (GC analysis)).

Example 24

Preparation of 4-thiophen-2-yl-pyridine

Using a THF solution of 2-thienylmagnesium bromide (3.00 mL, 1.00 M, 3.0 mmol) and 2-bromopyridine (316.0 mg, 2.0 mmol), CoF$_2$.4H$_2$O (20.3 mg, 0.12 mmol) and 1,3-bis(2,6-diisopropylphenyl)imidazolinium chloride (102.3 mg, 0.24 mmol) as starting materials, the reaction was performed at a scale of 2.0 mmol at 80° C. for 24 hours in the same manner as in Example 23. After performing silica gel column chromatography (ethyl acetate=5% in hexane), the above compound was obtained as a yellow solid (0.303 g, yield=94%, purity=>98% (GC analysis)).

Example 25

In the same manner as in Example 22, 4-methyl biphenyl was prepared using the catalysts, additives and reaction conditions shown in Table 1. In Tables 1 to 4, "mol %" represents a mol % relative to the organic halogen compound (3); Ph represents a phenyl group, and Tol represents a tolyl group; acac represents acetylacetonato and SIPr.HCl, IPr.HCl, IPr, I-t-Bu.HCl and PPh₃ represent the following compounds.

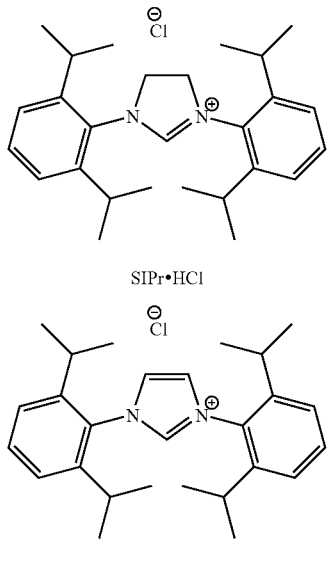

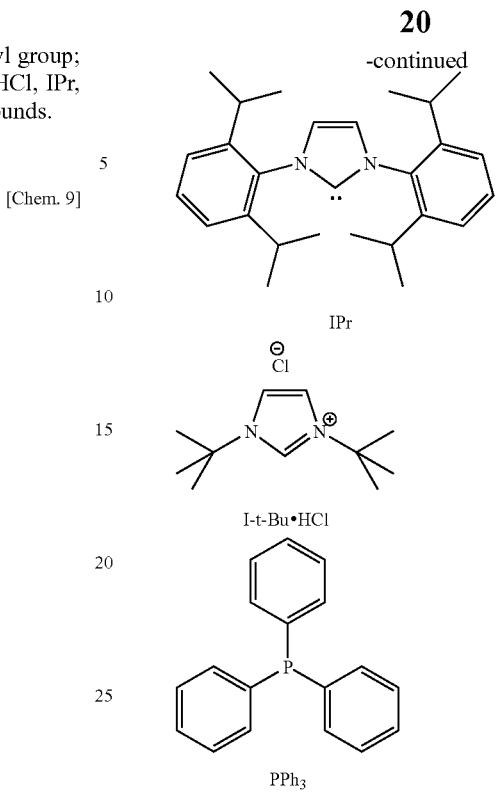

TABLE 1

| entry[a] | Fe/Co salt (mol %) | additives (mol %) | yield[b] (%) | | | |
|---|---|---|---|---|---|---|
| | | | 2 | 3 | 1 | 4[c] |
| 1 | FeF₃·3H₂O (5) | SIPr·HCl (15) | 98 | <1 | 0 | 4 |
| 2 | FeF₃·3H₂O (5) | SIPr·HCl (10) | 93 | 1 | 5 | 4 |
| 3 | FeF₂·4H₂O (5) | SIPr·HCl (15) | 96 | <1 | 0 | 5 |
| 4[d] | CoF₂·4H₂O (5) | SIPr·HCl (15) | 91 | <1 | 2 | 10 |
| 5[e] | CoF₂·4H₂O (3) | IPr·HCl (6) | 95 | 3 | 0 | 11 |
| 6[e] | CoF₂·4H₂O (3) | IPr (6) | 96 | 2 | 0 | 8 |
| 7[e] | CoCl₂·6H₂O (3) | IPr·HCl (6) | 68 | 11 | 2 | 15 |
| 8 | FeCl₃ (5), KF (20) | SIPr·HCl (15) | 92 | 1 | 0 | 8 |
| 9 | FeCl₃ (5) | SIPr·HCl (15) | 32 | 2 | 10 | 32 |
| 10 | Fe(acac)₃ | SIPr·HCl (15) | 26 | 2 | 18 | 29 |
| 11 | FeF₃·3H₂O | PPh₃ (5) | 2 | 0 | 94 | 4 |
| 12[d] | FeF₃·3H₂O | IPr·HCl (15) PPh₃ (5) | 92 | 3 | 4 | 9 |
| 13[d] | FeF₃·3H₂O | I-t-BuHCl (15) | 92 | 1 | 0 | 8 |

[a]The reaction was performed at a scale of 0.4 mmol.
[b]The yield was measured by GC analysis as the internal standard using undecane.
[c]The yield is based on the amount of p-tolylmagnesium bromide.
[d]The reaction was performed at 60° C. for 24 hours, and at 80° C. for 12 hours.
[e]The reaction was performed at 60° C. for 48 hours.

Example 26

In the same manner as in Example 2, the aromatic compounds shown in Table 2 were prepared using the materials and reaction conditions shown in Table 2.

TABLE 2

$$\text{R}^1\text{-X} + \text{R}^2\text{MgX} \xrightarrow[\text{SIPr·HCl (9 mol \%)}]{\text{FeF}_3\cdot 3\text{H}_2\text{O (3 mol \%)}} \xrightarrow[\text{THF, 0°C. then rt, 4~6 h}]{\text{EtMgBr (18 mol \%)}} \xrightarrow[\text{THF, 60°C., 24 h}]{\text{p-TolMgBr (1.2 eq), Ph-Cl (1.0 eq)}} \text{Ph-p-Tol} + \text{Ph-Ph} + \text{p-Tol-p-Tol}$$

2 (98%)  3 (trace)  4 (3%)

| entry[a] | R¹—X | R²MgX | yield[b] of R¹—R² (%) (conditions) |
|---|---|---|---|
| 1 | 4-MeO-C₆H₄-Cl | 4-Me-C₆H₄-MgBr | 92 (60°C., 24 h) |
| 2 | 2-MeO-C₆H₄-Cl | 2-Me-C₆H₄-MgBr | 90 (80°C., 24 h) |
| 3 | Ph-Cl | 2,4,6-Me₃-C₆H₂-MgBr | 93[c] (120°C., 24 h)[d] |
| 4[e] | 4-Bu-C₆H₄-Cl | 4-F-C₆H₄-MgBr | 87 (60°C., 24 h) |
| 5[f] | 2-MeO-C₆H₄-Cl | 1-naphthyl-MgBr (1.2) | 92 (70°C., 48 h) |
| 6 | 2-MeO-C₆H₄-Cl | 2-naphthyl-MgBr (1.5) | 96 (60°C., 24 h) |
| 7, 8 | 3-Me₂N-C₆H₄-Cl | Ph-MgX (1.2) | X = Br 94; X = I 93 (60°C., 24 h) |
| 9[g] | 4-MeS-C₆H₄-Cl | 4-Me-C₆H₄-MgBr (1.35) | 80 (60°C., 24 h) |

TABLE 2-continued $$\text{FeF}_3\cdot 3\text{H}_2\text{O (3 mol \%)} \atop \text{SIPr·HCl (9 mol \%)} \xrightarrow[\text{THF, 0° C. then rt, 4~6 h}]{\text{EtMgBr (18 mol \%)}} \xrightarrow[\text{THF, 60° C., 24 h}]{\text{p-TolMgBr (1.2 eq)} \atop \text{Ph-Cl (1.0 eq)}}$$

Ph-p-Tol + Ph-Ph + p-Tol-p-Tol
2 (98%)      3 (trace)    4 (3%)

| entry[a] | R¹—X | R²MgX | yield[b] of R¹—R² (%) (conditions) |
|---|---|---|---|
| 10 | 2-(4-chlorophenyl)-1,3-dioxolane | PhMgBr (1.35) | 88 (60°C., 24 h 80°C., 12 h) |
| 11 | 1-fluoro-4-chlorobenzene | 4-MeO-C₆H₄-MgBr (1.2) | 91 (60°C., 24 h) |
| 12[f] | 3,4-difluorochlorobenzene | 4-MeO-C₆H₄-MgBr (1.5) | 81 (60°C., 24 h 80°C., 12 h) |
| 13 | 2-bromopyridine | 2,4,6-trimethylphenyl-MgBr (1.2) | 76 (90°C., 24 h) |
| 14[g] | 2-bromopyridine | 2-thienyl-MgBr (1.5) | 74 (80°C., 24 h) |
| 15 | 2-chloroanisole | Et-MgBr | 94[c] (60°C., 24 h) |
| 16 | vinyl bromide (E:Z = 8:2) | 4-MeO-C₆H₄-MgBr (1.5) | 85[c] (60°C., 12 h) |

[a] The reaction was performed at a scale of 0.5 or 1.0 mmol.
[b] isolated yield.
[c] GC yield.
[d] The reaction was performed in toluene.
[e] 4 mol % of iron catalyst was used.
[f] 5 mol % of iron catalyst was used.
[g] 6 mol % of iron catalyst was used.

Example 27

In the same manner as in Example 15, the biphenyl compounds shown in Table 3 were prepared using the materials and reaction conditions shown in Table 3.

TABLE 3

FeF$_3$·3H$_2$O (5 mol %)
IPr·HCl (15 mol %)
PPh$_3$ (5 mol %)

EtMgBr (35 mol %)
THF, 0° C. then rt, 6 h
→
p-TolMgBr (1.5 eq)
Ph-Cl (1.0 eq)
THF, 60° C., 24 h then 80° C., 12 h
→

Ph-p-Tol + Ph-Ph + p-Tol-p-Tol
2 (93%)    3 (6%)    4 (12%)

| entry[a] | Ar$^1$—X | Ar$^2$MgX | yield[b] of Ar$^1$—Ar$^2$ (%) |
|---|---|---|---|
| 1 | MeO—C$_6$H$_4$—Cl | p-Tol-MgX (1.5) | X = Br 90 |
| 2 | | | X = I 89 |
| 3 | 2-MeO-C$_6$H$_4$-Cl | o-Tol-MgBr (1.5) | 95 |
| 4[c] | Ph-Cl | 2,4,6-Me$_3$C$_6$H$_2$-MgBr (1.5) | 91[d] |
| 5 | 4-Bu-C$_6$H$_4$-Cl | 4-F-C$_6$H$_4$-MgBr (1.5) | 88 |
| 6[e] | 4-Bu-C$_6$H$_4$-Cl | 3,4-F$_2$-C$_6$H$_3$-MgBr (3.0) | 84[d] |
| 7 | 2-MeO-C$_6$H$_4$-Cl | 1-Naphthyl-MgBr (1.5) | 92 |
| 8 | 3-Me$_2$N-C$_6$H$_4$-Cl | Ph-MgBr (1.5) | 89 |

TABLE 3-continued $FeF_3 \cdot 3H_2O$ (5 mol %), IPr·HCl (15 mol %), PPh$_3$ (5 mol %); EtMgBr (35 mol %), THF, 0° C. then rt, 6 h; p-TolMgBr (1.5 eq), Ph-Cl (1.0 eq), THF, 60° C., 24 h then 80° C., 12 h → Ph-p-Tol 2 (93%) + Ph-Ph 3 (6%) + p-Tol-p-Tol 4 (12%)

| entry[a] | Ar$^1$—X | Ar$^2$MgX | yield[b] of Ar$^1$—Ar$^2$ (%) |
|---|---|---|---|
| 9 | 4-F-C$_6$H$_4$—Cl | 4-MeO-C$_6$H$_4$—MgBr (1.5) | 82 |
| 10 | 2-F-C$_6$H$_4$—Cl | 4-MeO-C$_6$H$_4$—MgBr (1.5) | 68 |
| 11[f] | 2-pyridyl—X | 2,4,6-trimethylphenyl—MgBr (1.5) | X = Cl 70 |
| 12[f] | 2-pyridyl—X | 2,4,6-trimethylphenyl—MgBr (1.5) | X = Br 90 |
| 13[g] | 2-pyridyl—Br | 2-thienyl—MgBr (1.5) | 83 |

[a] The reaction was performed at a scale of 0.5 to 1.0 mmol.
[b] isolated yield.
[c] The reaction was performed in toluene at 120° C. for 36 hours, using 7 mol % of iron catalyst.
[d] GC yield.
[e] 15 mol % of iron catalyst was used.
[f] The reaction was performed in toluene at 100° C. for 12 hours.
[g] The reaction was performed at 60° C. for 36 hours, using 7 mol % of iron catalyst.

Example 28

In the same manner as in Example 15, the biphenyl compound shown in Table 4 was prepared using the materials and reaction conditions shown in Table 4.

TABLE 4

$CoF_2 \cdot 4H_2O$ (X mol %), IPr·HCl (2X mol %); EtMgBr (6X mol %), THF, 0° C. then rt, 4 h; Ar$^1$—X (1.0 eq), Ar$^2$MgBr (1.2-1.5 eq), THF, 60° C., 24 h → Ar$^1$—Ar$^2$ yield (%)

| entry[a] | Ar$^1$—X | Ar$^2$MgBr | yield[b] of Ar$^1$—Ar$^2$ (%) X mol % (conditions) |
|---|---|---|---|
| 1 | 4-MeO-C$_6$H$_4$—Cl | C$_6$H$_5$—MgBr (1.2) | 94, 3 mol % (60° C., 24 h) |

TABLE 4-continued $$\text{CoF}_2 \cdot 4\text{H}_2\text{O (X mol \%)}, \text{IPr} \cdot \text{HCl (2X mol \%)}, \text{EtMgBr (6X mol \%)}, \text{THF, 0° C. then rt, 4 h} \xrightarrow{\text{Ar}^1\text{—X (1.0 eq)}, \text{Ar}^2\text{MgBr (1.2-1.5 eq)}, \text{THF, 60° C., 24 h}} \text{Ar}^1\text{—Ar}^2 \text{ yield (\%)}$$

| entry[a] | Ar¹—X | Ar²MgBr | yield[b] of Ar¹—Ar² (%) X mol % (conditions) |
|---|---|---|---|
| 2 | MeO—C₆H₄—Br | 2,4,6-trimethylphenyl-MgBr (1.2) | 84, 3 mol %, (80° C., 24 h) |
| 3 | Bu—C₆H₄—Cl | F—C₆H₄—MgBr (1.5) | 86, 4 mol %, (60° C., 24 h) |
| 4 | 3,4-difluoro-C₆H₃—Cl | MeO—C₆H₄—MgBr (1.5) | 97, 5 mol %, (60° C., 24 h) |
| 5 | 2-(but-3-en-1-yl)-C₆H₄—Br | 4-Me-C₆H₄—MgBr (1.2) | 82, 1 mol %, (60° C., 4 h) |
| 6 | 2-thienyl—Cl | MeO—C₆H₄—MgBr (1.5) | 95, 2 mol %, (50° C., 15 h) |
| 7 | 3-thienyl—Br | 4-Me-C₆H₄—MgBr (1.2) | 95, 2 mol %, (50° C., 15 h) |
| 8 | 2-pyridyl—Br | 2-thienyl—MgBr (1.5) | 94, 6 mol %, (60° C., 18 h) |

[a] The reaction was performed at a scale of 1.0 to 2.0 mmol.
[b] isolated yield.

Example 29

Preparation of 4-methylbiphenyl

A methanol solution of KF (0.64 mL, 0.50 M, 0.32 mmol) was added to a THF solution of FeCl₃ (0.80 mL, 0.10 M, 0.08 mmol) at 0° C. under argon atmosphere. The following process was also performed under argon atmosphere. After stirring for fifteen minutes, THF and methanol were removed under reduced pressure, and 1,3-bis(2,6-diisopropylphenyl) imidazolinium chloride (102.5 mg, 0.24 mmol), chlorobenzene (180.1 mg, 1.6 mmol), and a THF solution of p-tolylmagnesium bromide (3.54 mL, 1.13 M, 4.0 mmol) were added to the mixture. THF (0.50 mL) was added to rinse the internal wall of the reaction vessel. The mixture was reacted for 24 hours at 60° C. After cooled to the ambient temperature, 2.0 mL of saturated sodium potassium tartrate aqueous solution was added to the reaction mixture. The water layer was extracted five times using Et₂O. The total organic extract was filtrated by Florisil pad (100-200 mesh, Nacalai Tesque, Inc.). As the internal standard, gas chromatographic analysis was performed using undecane (84.4 μL, 0.4 mmol) (yield=92%). After removing the solvent under reduced pressure, the crude product was purified by silica gel chromatography (pentane), thereby obtaining the above compound, which was a colorless liquid (0.247 g, yield=92%, >98% purity (GC analysis)).

The invention claimed is:

1. A catalyst composition for a cross-coupling reaction comprising an iron or cobalt fluoride and a nitrogen-containing heterocyclic compound represented by Formula (1A),

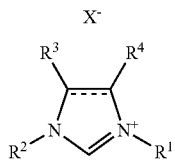
(1A)

wherein
$R^1$ and $R^2$ are same or different, and represent substituted or unsubstituted aryl group, heteroaryl group, alkyl group, cycloalkyl group, or adamantyl group;
$R^3$ and $R^4$ are same or different, and represent hydrogen, substituted or unsubstituted aryl group, heteroaryl group, alkyl group, cycloalkyl group, adamantyl group, alkoxy group, or silyl group having three substituents selected from the group consisting of alkyl groups and aryl groups;
$R^3$ and $R^4$, taken with the carbon atoms to which they are attached, may form a saturated or unsaturated ring structure comprising carbons and/or one or more hetero elements;
------ represents a single bond or a double bond, and
$X^-$ represents a monovalent anion, and
wherein the catalyst composition does not comprise a nickel catalyst.

2. A catalyst composition for a cross-coupling reaction comprising an iron or cobalt fluoride and a nitrogen-containing heterocyclic compound represented by Formula (1B),

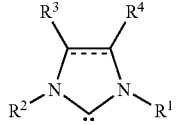
(1B)

wherein
$R^1$ and $R^2$ are same or different, and represent substituted or unsubstituted aryl group, heteroaryl group, alkyl group, cycloalkyl group, or adamantyl group;
$R^3$ and $R^4$ are same or different, and represent hydrogen, substituted or unsubstituted aryl group, heteroaryl group, alkyl group, cycloalkyl group, adamantyl group, alkoxy group, or silyl group having three substituents selected from the group consisting of alkyl groups and aryl groups;
$R^3$ and $R^4$, taken with the carbon atoms to which they are attached, may form a saturated or unsaturated ring structure comprising carbons and/or one or more hetero elements;
------ represents a single bond or a double bond, and
$X^-$ represents a monovalent anion, and
wherein the catalyst composition does not comprise a nickel catalyst.

3. A method for producing a cross-coupling compound, represented by Formula (4), $$R^5—R^6 \qquad (4)$$

wherein $R^5$ and $R^6$ each represent substituted or unsubstituted aryl group, substituted or unsubstituted heteroaryl group, or alkyl group,
the method comprising the step of:
subjecting an organic magnesium compound represented by Formula (2), $$R^5—MgY_1 \qquad (2)$$

wherein $R^5$ is as defined above, and $Y_1$ represents halogen; and
an organic halogen compound represented by Formula (3), $$R^6—Y_2 \qquad (3)$$

wherein $R^6$ is as defined above, and $Y_2$ represents halogen or $R^5$,
to a cross-coupling reaction in the presence of the catalyst composition according to claim 1.

4. The method of claim 3, wherein the cross-coupling reaction is performed by adding a deprotonating agent to a reaction system.

5. The method of claim 4, wherein the deprotonating agent is an organic metallic compound, metal hydride compound, metal alkoxide or metal amide.

6. The method of claim 3, wherein $R^5$ and $R^6$ are different.

7. The method of claim 3, wherein the iron or cobalt fluoride is $FeF_2$, $FeF_3$, $FeClF_2$, $FeF_6$, $CoF_2$ or $CoF_3$.

8. The method of claim 4, wherein $R^5$ and $R^6$ are different.

9. The method of claim 8, wherein the iron or cobalt fluoride is $FeF_2$, $FeF_3$, $FeClF_2$, $FeF_6$, $CoF_2$ or $CoF_3$.

10. The method of claim 5, wherein $R^5$ and $R^6$ are different.

11. The method of claim 10, wherein the iron or cobalt fluoride is $FeF_2$, $FeF_3$, $FeClF_2$, $FeF_6$, $CoF_2$ or $CoF_3$.

12. A method for producing a cross-coupling compound, represented by Formula (4), $$R^5—R^6 \qquad (4)$$

wherein $R^5$ and $R^6$ each represent substituted or unsubstituted aryl group, substituted or unsubstituted heteroaryl group, or alkyl group,
the method comprising the step of:
subjecting an organic magnesium compound represented by Formula (2), $$R^5—MgY_1 \qquad (2)$$

wherein $R^5$ is as defined above, and $Y_1$ represents halogen; and
an organic halogen compound represented by Formula (3), $$R^6—Y_2 \qquad (3)$$

wherein $R^6$ is as defined above, and $Y_2$ represents halogen or $R^5$,
to a cross-coupling reaction in the presence of the catalyst composition according to claim 2.

13. The method of claim 12, wherein the cross-coupling reaction is performed by adding a deprotonating agent to a reaction system.

14. The method of claim 13, wherein the deprotonating agent is an organic metallic compound, metal hydride compound, metal alkoxide or metal amide.

15. The method of claim 12, wherein $R^5$ and $R^6$ are different.

16. The method of claim 12, wherein the iron or cobalt fluoride is $FeF_2$, $FeF_3$, $FeClF_2$, $FeF_6$, $CoF_2$ or $CoF_3$.

17. The method of claim 13, wherein $R^5$ and $R^6$ are different.

18. The method of claim 17, wherein the iron or cobalt fluoride is $FeF_2$, $FeF_3$, $FeClF_2$, $FeF_6$, $CoF_2$ or $CoF_3$.

19. The method of claim 14, wherein $R^5$ and $R^6$ are different.

20. The method of claim 19, wherein the iron or cobalt fluoride is $FeF_2$, $FeF_3$, $FeClF_2$, $FeF_6$, $CoF_2$ or $CoF_3$.

* * * * *